United States Patent
Niwa et al.

(10) Patent No.: US 6,197,562 B1
(45) Date of Patent: Mar. 6, 2001

(54) L-SORBOSE DEHYDROGENASE AND NOVEL L-SORBOSONE DEHYDROGENASE OBTAINED FROM GLUCONOBACTER OXYDANS T-100

(75) Inventors: Mineo Niwa, Muko; Yoshimasa Saito, Kawanishi; Yoshinori Ishii, Kobe; Masaru Yoshida, Hoi-gun; Hiromi Suzuki, Owariasahi, all of (JP)

(73) Assignee: Fujisawa Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 09/118,317

(22) Filed: Jul. 17, 1998

Related U.S. Application Data

(62) Continuation of application No. 08/942,673, filed on Oct. 2, 1997, now Pat. No. 5,861,292, which is a continuation of application No. 08/513,841, filed as application No. PCT/JP94/00369 on Mar. 8, 1994, now Pat. No. 5,753,481.

(30) Foreign Application Priority Data

Mar. 8, 1993 (GB) ..... 9304700
Sep. 28, 1993 (JP) ..... 5-241851

(51) Int. Cl.[7] ............... C12N 9/04; C12N 9/02
(52) U.S. Cl. ............... 435/190; 435/189
(58) Field of Search ............... 435/189, 190

(56) References Cited

U.S. PATENT DOCUMENTS 4,902,617 * 2/1990 Fujiwara et al. ............... 435/138

* cited by examiner

*Primary Examiner*—Elizabeth Slobodyansky
(74) *Attorney, Agent, or Firm*—Oblon, Spivak, McClelland, Maier & Neustadt, P.C.

(57) ABSTRACT

A novel L-sorbose dehydrogenase (SDH) and a novel L-sorbosone dehydrogenase both derived from Gluconobacter oxydans T-100, a DNA which encodes the SDH and/or SNDH, an expression vector which contains the DNA, a host cell transformed by the expression vector and a process for producing the SDH and/or SNDH, which comprises culturing the host cell in a medium and recovering the SDH and/or SNDH from the resulting culture. The SDH and SNDH of the present invention are useful enzymes having preferable properties for the production of 2-keto-L-gulonic acid, as well as L-ascorbic acid. According to the production method of the present invention, the SDH and SNDH having such preferable properties can be produced in large amounts by genetic engineering.

2 Claims, 3 Drawing Sheets

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
      (A) LENGTH: 530 amino acids
      (B) TYPE: amino acid
      (D) TOPOLOGY: linear (ii) MOLECULE TYPE: peptide (vi) ORIGINAL SOURCE:
      (A) ORGANISM: Gluconobacter oxydans
      (B) STRAIN: T-100

(ix) FEATURE:
      (A) NAME/KEY: mat peptide
      (B) LOCATION: 1..530
      (C) IDENTIFICATION METHOD: experimentally (xi) SEQUENCE DESCRIPTION: SEQ ID NO: 1:

```
Thr Ser Gly Phe Asp Tyr Ile Val Val Gly Gly Gly Ser Ala Gly
  1               5                  10                  15

Cys Val Leu Ala Ala Arg Leu Ser Glu Asn Pro Ser Val Arg Val
                 20                  25                  30

Cys Leu Ile Glu Ala Gly Arg Arg Asp Thr His Pro Leu Ile His
                 35                  40                  45

Met Pro Val Gly Phe Ala Lys Met Thr Thr Gly Pro His Thr Trp
                 50                  55                  60

Asp Leu Leu Thr Glu Pro Gln Lys His Ala Asn Asn Arg Gln Ile
                 65                  70                  75

Pro Tyr Val Gln Gly Arg Ile Leu Gly Gly Ser Ser Ile Asn
                 80                  85                  90

Ala Glu Val Phe Thr Arg Gly His Pro Ser Asp Phe Asp Arg Trp
                 95                 100                 105

Ala Ala Glu Gly Ala Asp Gly Trp Ser Phe Arg Asp Val Gln Lys
                110                 115                 120
```

```
Tyr Phe Ile Arg Ser Glu Gly Asn Ala Val Phe Ser Gly Thr Trp
            125                 130                 135

His Gly Thr Asn Gly Pro Leu Gly Val Ser Asn Leu Ala Glu Pro
            140                 145                 150

Asn Pro Thr Ser Arg Ala Phe Val Gln Ser Cys Gln Glu Met Gly
            155                 160                 165

Leu Pro Tyr Asn Pro Asp Phe Asn Gly Ala Ser Gln Glu Gly Ala
            170                 175                 180

Gly Ile Tyr Gln Met Thr Ile Arg Asn Arg Arg Cys Ser Thr
            185                 190                 195

Ala Val Gly Tyr Leu Arg Pro Ala Leu Gly Arg Lys Asn Leu Thr
            200                 205                 210

Val Val Thr Arg Ala Leu Val Leu Lys Ile Val Phe Asn Gly Thr
            215                 220                 225

Arg Ala Thr Gly Val Gln Tyr Ile Ala Asn Gly Thr Leu Asn Thr
            230                 235                 240

Ala Glu Ala Ser Gln Glu Ile Val Val Thr Ala Gly Ala Ile Gly
            245                 250                 255

Thr Pro Lys Leu Met Met Leu Ser Gly Val Gly Pro Ala Ala His
            260                 265                 270

Leu Arg Glu Asn Gly Ile Pro Val Val Gln Asp Leu Pro Gly Val
            275                 280                 285

Gly Glu Asn Leu Gln Asp His Phe Gly Val Asp Ile Val Ala Glu
            290                 295                 300

Leu Lys Thr Asp Glu Ser Phe Asp Lys Tyr Arg Lys Leu His Trp
            305                 310                 315

Met Leu Trp Ala Gly Leu Glu Tyr Thr Met Phe Arg Ser Gly Pro
            320                 325                 330

Val Ala Ser Asn Val Val Glu Gly Gly Ala Phe Trp Tyr Ser Asp
            335                 340                 345

Pro Ser Ser Gly Val Pro Asp Leu Gln Phe His Phe Leu Ala Glu
            350                 355                 360

Ala Gly Ala Glu Ala Gly Val Thr Ser Val Pro Lys Gly Ala Ser
            365                 370                 375

Gly Ile Thr Leu Asn Ser Tyr Val Leu Arg Pro Lys Ser Arg Gly
            380                 385                 390

Thr Val Arg Leu Arg Ser Ala Asp Pro Arg Val Asn Pro Met Val
            395                 400                 405

Asp Pro Asn Phe Leu Gly Asp Pro Ala Asp Leu Glu Thr Ser Ala
            410                 415                 420

Glu Gly Val Arg Leu Ser Tyr Glu Met Phe Ser Gln Pro Ser Leu
            425                 430                 435

Glu Lys His Ile Arg Lys Thr Cys Phe Phe Ser Gly Lys Gln Pro
            440                 445                 450

Thr Met Gln Met Tyr Arg Asp Tyr Ala Arg Glu His Gly Arg Thr
            455                 460                 465

Ser Tyr His Pro Thr Cys Thr Cys Lys Met Gly Arg Asp Asp Met
            470                 475                 480

Ser Val Val Asp Pro Arg Leu Lys Val His Gly Leu Glu Gly Ile
            485                 490                 495

Arg Ile Cys Asp Ser Ser Val Met Pro Ser Leu Leu Gly Ser Asn
            500                 505                 510
```

```
Thr Asn Ala Ala Thr Ile Met Ile Ser Glu Arg Ala Ala Asp Phe
                515                 520                 525

Ile Gln Gly Asn Ala
                530

(2) INFORMATION FOR SEQ ID NO: 2:

(i) SEQUENCE CHARACTERISTICS:
        (A) LENGTH: 497 amino acids
        (B) TYPE: amino acid
        (D) TOPOLOGY: linear (ii) MOLECULE TYPE: peptide (vi) ORIGINAL SOURCE:
        (A) ORGANISM: Gluconobacter oxydans
        (B) STRAIN: T-100

(ix) FEATURE:
        (A) NAME/KEY: mat peptide
        (B) LOCATION: 1..497
        (C) IDENTIFICATION METHOD: experimentally (xi) SEQUENCE DESCRIPTION: SEQ ID NO: 2:

Asn Val Val Ser Lys Thr Val Ser Leu Pro Leu Lys Pro Arg Glu
 1               5                  10                  15

Phe Gly Phe Phe Ile Asp Gly Glu Trp Arg Ala Gly Lys Asp Phe
                20                  25                  30

Phe Asp Arg Ser Ser Pro Ala His Asp Val Pro Val Thr Arg Ile
                35                  40                  45

Pro Arg Cys Thr Arg Glu Asp Leu Asp Glu Ala Val Ala Ala Ala
                50                  55                  60

Arg Arg Ala Phe Glu Asn Gly Ser Trp Ala Gly Leu Ala Ala Ala
                65                  70                  75

Asp Arg Ala Ala Val Leu Leu Lys Ala Ala Gly Leu Leu Arg Glu
                80                  85                  90

Arg Arg Asp Asp Ile Ala Tyr Trp Glu Val Leu Glu Asn Gly Lys
                95                  100                 105

Pro Ile Ser Gln Ala Lys Gly Glu Ile Asp His Cys Ile Ala Cys
                110                 115                 120

Phe Glu Met Ala Ala Gly Ala Ala Arg Met Leu His Gly Asp Thr
                125                 130                 135

Phe Asn Asn Leu Gly Glu Gly Leu Phe Gly Met Val Leu Arg Glu
                140                 145                 150

Pro Ile Gly Val Val Gly Leu Ile Thr Pro Trp Asn Phe Pro Phe
                155                 160                 165

Met Ile Leu Cys Glu Arg Ala Pro Phe Ile Leu Ala Ser Gly Cys
                170                 175                 180

Thr Leu Val Val Lys Pro Ala Glu Val Thr Ser Ala Thr Thr Leu
                185                 190                 195

Leu Leu Ala Glu Ile Leu Ala Asp Ala Gly Leu Pro Lys Gly Val
                200                 205                 210

Phe Asn Val Val Thr Gly Thr Gly Arg Thr Val Gly Gln Ala Met
                215                 220                 225

Thr Glu His Gln Asp Ile Asp Met Leu Ser Phe Thr Gly Ser Thr
                230                 235                 240

Gly Val Gly Lys Ser Cys Ile His Ala Ala Ala Asp Ser Asn Leu
                245                 250                 255

Lys Lys Leu Gly Leu Glu Leu Gly Gly Lys Asn Pro Ile Val Val
```

```
                        260                 265                 270
Phe Ala Asp Ser Asn Leu Glu Asp Ala Ala Asp Ala Val Ala Phe
                275                 280                 285
Gly Ile Ser Phe Asn Thr Gly Gln Cys Cys Val Ser Ser Ser Arg
                290                 295                 300
Leu Ile Val Glu Arg Ser Val Ala Glu Lys Phe Glu Arg Leu Val
                305                 310                 315
Val Pro Lys Met Glu Lys Ile Arg Val Gly Asp Pro Phe Asp Pro
                320                 325                 330
Glu Thr Gln Ile Gly Ala Ile Thr Thr Glu Ala Gln Asn Lys Thr
                335                 340                 345
Ile Leu Asp Tyr Ile Ala Lys Gly Lys Ala Glu Gly Ala Lys Leu
                350                 355                 360
Leu Cys Gly Gly Gly Ile Val Asp Phe Gly Lys Gly Gln Tyr Ile
                365                 370                 375
Gln Pro Thr Leu Phe Thr Asp Val Lys Pro Ser Met Gly Ile Ala
                380                 385                 390
Arg Asp Glu Ile Phe Gly Pro Val Leu Ala Ser Phe His Phe Asp
                395                 400                 405
Thr Val Asp Glu Ala Ile Ala Ile Ala Asn Asp Thr Val Tyr Gly
                410                 415                 420
Leu Ala Ala Ser Val Trp Ser Lys Asp Ile Asp Lys Ala Leu Ala
                425                 430                 435
Val Thr Arg Arg Val Arg Ala Gly Arg Phe Trp Val Asn Thr Ile
                440                 445                 450
Met Ser Gly Gly Pro Glu Thr Pro Leu Gly Gly Phe Lys Gln Ser
                455                 460                 465
Gly Trp Gly Arg Glu Ala Gly Leu Tyr Gly Val Glu Glu Tyr Thr
                470                 475                 480
Gln Ile Lys Ser Val His Ile Glu Thr Gly Lys Arg Ser His Trp
                485                 490                 495
Ile Ser (2) INFORMATION FOR SEQ ID NO: 3:

(i) SEQUENCE CHARACTERISTICS:
        (A) LENGTH: 1596 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Gluconobacter oxydans
        (B) STRAIN: T-100

(ix) FEATURE:
        (A) NAME/KEY: CDS
        (B) LOCATION: 4..1593
        (C) IDENTIFICATION METHOD: experimentally (xi) SEQUENCE DESCRIPTION: SEQ ID NO: 3:

ATGACGAGCG GTTTTGATTA CATCGTTGTC GGTGGCGGTT CGGCTGGCTG TGTTCTCGCA    60

GCCCGCCTTT CCGAAAATCC TTCCGTCCGT GTCTGTCTCA TCGAGGCGGG CCGGCGGGAC   120

ACGCATCCCC TGATCCACAT GCCGGTCGGT TTCGCGAAGA TGACCACGGG GCCGCATACC   180

TGGGATCTTC TGACGGAGCC GCAGAAACAT GCGAACAACC GCCAGATCCC CTATGTGCAG   240
```

-continued

```
GGCCGGATTC TGGGCGGCGG ATCGTCCATC AACGCGGAAG TCTTCACGCG GGACACCCT    300

TCCGACTTCG ACCGCTGGGC GGCGGAAGGT GCGGATGGCT GGAGCTTCCG GGATGTCCAG   360

AAGTACTTCA TCCGTTCCGA AGGCAATGCC GTGTTTTCGG GCACCTGGCA TGGCACGAAC   420

GGGCCGCTCG GGGTGTCCAA CCTCGCGGAG CCGAACCCGA CCAGCCGTGC CTTCGTGCAG   480

AGCTGTCAGG AAATGGGGCT GCCCTACAAC CCTGACTTCA ACGGCGCATC GCAGGAAGGC   540

GCAGGCATCT ATCAGATGAC GATCCGCAAC AACCGGCGCT GCTCGACGGC TGTGGGGTAT   600

CTGCGTCCGG CTCTGGGCG GAAGAACCTG ACGGTTGTGA CGCGGGCGCT GGTCCTGAAG    660

ATCGTCTTCA ACGGAACGCG GGCGACGGGC GTGCAGTATA TCGCCAACGG CACCCTGAAT   720

ACCGCCGAAG CGAGCCAGGA AATCGTTGTG ACGGCCGGAG CGATCGGAAC GCCGAAGCTG   780

ATGATGCTGT CGGGCGTCGG GCCTGCCGCG CATCTTCGCG AAAATGGTAT CCCGGTCGTG   840

CAGGATCTGC CGGGCGTGGG CGAGAACCTT CAGGATCATT TCGGTGTGGA TATCGTAGCC   900

GAGCTCAAGA CGGATGAGAG CTTCGACAAG TACCGAAAC TGCACTGGAT GCTGTGGGCA    960

GGTCTTGAAT ATACCATGTT CAGATCCGGT CCCGTTGCAT CCAACGTGGT TGAGGGCGGC  1020

GCGTTCTGGT ACTCGGACCC GTCATCGGGT GTTCCTGATC TCCAGTTCCA TTTTCTTGCG  1080

GAGGCTGGGG CTGAGGCTGG AGTGACGTCC GTTCCCAAGG GAGCGTCCGG GATTACGCTG  1140

AACAGCTATG TGCTGCGTCC GAAGTCTCGT GGAACTGTCC GGCTGCGTTC GGCAGATCCA  1200

AGGGTCAATC CGATGGTCGA TCCCAATTTC CTTGGAGACC CGGCCGACCT TGAGACGTCT  1260

GCGGAAGGTG TGCGCCTGAG CTACGAGATG TTCTCCCAGC CGTCTTTGGA GAAGCACATC  1320

CGGAAAACCT GTTTCTTTAG CGGTAAACAG CCGACGATGC AGATGTATCG GGACTATGCG  1380

CGGGAACATG GCCGGACGTC CTATCATCCG ACATGCACCT GCAAGATGGG TCGTGATGAC  1440

ATGTCCGTCG TCGATCCGCG TCTGAAGGTT CATGGCCTTG AGGGCATCAG GATCTGTGAC  1500

AGTTCGGTTA TGCCGTCGCT GCTCGGTTCC AACACCAATG CTGCGACGAT CATGATCAGT  1560

GAGCGGGCAG CGGATTTCAT TCAGGGGAAC GCCTGA                           1596
```

(2) INFORMATION FOR SEQ ID NO: 4:

(i) SEQUENCE CHARACTERISTICS:
        (A) LENGTH: 1497 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Gluconobacter oxydans
        (B) STRAIN: T-100

(ix) FEATURE:
        (A) NAME/KEY: CDS
        (B) LOCATION: 4..1494
        (C) IDENTIFICATION METHOD: experimentally (xi) SEQUENCE DESCRIPTION: SEQ ID NO: 4:

```
ATGAATGTTG TCTCAAAGAC TGTATCTTTA CCGTTAAAGC CGCGTGAGTT CGGATTCTTT    60

ATTGATGGAG AATGGCGCGC AGGTAAGGAT TTCTTCGATC GTTCCTCGCC GGCTCATGAT   120

GTTCCCGTCA CCCGTATTCC ACGCTGCACC CGTGAAGACC TTGATGAGGC AGTCGCTGCT   180

GCACGTCGTG CTTTCGAGAA CGGAAGCTGG GCGGGTCTGG CAGCCGCGGA TCGTGCGGCG   240

GTTCTTCTGA AAGCCGCGGG CCTTCTGCGC GAGCGCCGTG ATGACATCGC TTACTGGGAA   300

GTTCTCGAAA ACGGGAAGCC CATCAGCCAG GCGAAAGGTG AGATCGATCA CTGTATCGCC   360
```

```
TGTTTCGAGA TGGCGGCCGG CGCTGCGCGG ATGCTGCATG GTGATACGTT CAACAATCTG      420

GGCGAGGGGC TGTTTGGCAT GGTCCTGCGG GAGCCCATCG GTGTCGTCGG TCTGATTACG      480

CCGTGGAACT TCCCGTTCAT GATCCTGTGT GAGCGGGCGC CTTTCATTCT CGCATCCGGC      540

TGCACGCTGG TCGTCAAGCC TGCCGAAGTC ACGAGTGCCA CGACCCTTCT TCTGGCAGAA      600

ATCCTTGCCG ATGCCGGGCT GCCGAAGGGT GTCTTCAATG TCGTGACAGG CACGGGGCGC      660

ACGGTCGGTC AGGCCATGAC CGAGCATCAG GATATCGACA TGCTGTCCTT CACGGGCTCC      720

ACGGGCGTCG GCAAGTCCTG TATCCACGCG GCGGCTGACA GCAACCTGAA GAAACTTGGC      780

CTCGAACTGG GCGGCAAGAA CCCGATTGTC GTGTTCGCTG ACAGCAACCT TGAGGATGCG      840

GCCGACGCGG TAGCCTTCGG GATCAGCTTT AATACCGGGC AGTGCTGTGT GTCGTCGAGC      900

CGCCTGATCG TAGAGCGGTC CGTGGCGGAG AAGTTCGAGC GCCTCGTCGT GCCAAAAATG      960

GAGAAGATCC GCGTTGGTGA TCCGTTTGAT CCCGAAACGC AGATTGGCGC CATCACGACG     1020

GAAGCGCAGA ACAAGACCAT TCTGGACTAT ATCGCGAAAG GCAAGGCCGA GGGCGCCAAG     1080

CTGCTCTGTG GTGGCGGGAT CGTCGATTTC GGCAAGGGAC AGTATATCCA GCCCACGCTT     1140

TTCACGGATG TGAAGCCCTC GATGGGCATC GCGCGTGACG AGATTTTTGG GCCGGTTCTG     1200

GCGTCCTTCC ACTTCGATAC CGTCGATGAG GCGATCGCGA TTGCCAATGA CACGGTTTAC     1260

GGCTTGGCCG CATCGGTCTG GAGCAAGGAT ATCGACAAGG CGCTTGCCGT GACCCGTCGT     1320

GTTCGTGCCG GCCGCTTCTG GGTGAACACC ATCATGAGCG GTGGTCCCGA GACGCCGCTG     1380

GGTGGTTTCA GCAGTCGGG CTGGGGCCGT GAGGCCGGTC TGTACGGCGT TGAGGAATAT     1440

ACGCAGATCA AATCTGTCCA TATCGAAACT GGCAAACGTT CGCACTGGAT TTCGTAA       1497

(2) INFORMATION FOR SEQ ID NO: 5:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO: 5:

Thr Ser Gly Phe Asp Tyr Ile Val Val Gly Gly Gly Ser Ala
 1               5                  10

(2) INFORMATION FOR SEQ ID NO: 6:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO: 6:

Asn Val Val Ser Lys Thr Val Xaa Leu
 1               5

(2) INFORMATION FOR SEQ ID NO: 7:

(i) SEQUENCE CHARACTERISTICS:
        (A) LENGTH: 16 amino acids
        (B) TYPE: amino acid
        (D) TOPOLOGY: linear (ii) MOLECULE TYPE: peptide
```

(xi) SEQUENCE DESCRIPTION: SEQ ID NO: 7:

Met Thr Thr Gly Pro His Thr Trp Asp Leu Leu Thr Glu Pro Gln Lys
  1               5                  10                  15

(2) INFORMATION FOR SEQ ID NO: 8:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 8:

Leu Met Met Leu Ser Gly Val Gly Pro Ala
  1               5                  10

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 9:

ACCWSCGGCT TYGAYTAYAT HGT                                       23

(2) INFORMATION FOR SEQ ID NO: 10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 10:

TCCCANGTRT GNGGNCC                                              17

(2) INFORMATION FOR SEQ ID NO: 11:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 11:

CTGTGTTCTC GC                                                   12

(2) INFORMATION FOR SEQ ID NO: 12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 12:

TCGGTTTCGC GAAGA                                                15

(2) INFORMATION FOR SEQ ID NO: 13:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 13:

CGTCTTCAAC GGAACG                                      16

(2) INFORMATION FOR SEQ ID NO: 14:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 14:

GGAGTGACGT CCGTTC                                      16

(2) INFORMATION FOR SEQ ID NO: 15:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 15:

GAGATGTTCT CCCAGC                                      16

(2) INFORMATION FOR SEQ ID NO: 16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 16:

TGATGGAGAA TGGCG                                       15

(2) INFORMATION FOR SEQ ID NO: 17:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 17:

GTAATCAGAC CGACG                                       15

(2) INFORMATION FOR SEQ ID NO: 18:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: other nucleic acid (synthetic DNA)

(xi) SEQUENCE DESCRIPTION: SEQ ID NO: 18:

TTCATTCTCG CATCC                                                        15

(2) INFORMATION FOR SEQ ID NO: 19:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 19:

GATCTCACCT TTCGC                                                        15

(2) INFORMATION FOR SEQ ID NO: 20:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 20:

CACGGATGTG AAGCC                                                        15

(2) INFORMATION FOR SEQ ID NO: 21:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 21:

GATCCTGTGT GAGCG                                                        15

(2) INFORMATION FOR SEQ ID NO: 22:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid (synthetic DNA)

(xi) SEQUENCE DESCRIPTION: SEQ ID NO: 22:

GCGATGTCAT CACGG                                                        15

L-SORBOSE DEHYDROGENASE AND NOVEL L-SORBOSONE DEHYDROGENASE OBTAINED FROM GLUCONOBACTER OXYDANS T-100

This application is a Continuation of application Ser. No. 08/942,673, filed on Oct. 2, 1997, now U.S. Pat. No. 5,861,292, which is a Continuation of application Ser. No. 08/513,841, filed on Nov. 1, 1995, now U.S. Pat. No. 5,753,481, which was filed as International Application No. PCT/JP94/00369, filed on Mar. 8, 1994.

TECHNICAL FIELD

The present invention relates to a novel L-sorbose dehydrogenase (hereinafter referred to as SDH) and a novel L-sorbosone dehydrogenase (hereinafter referred to as SNDH) both derived from *Gluconobacter Oxydans* T-100. More particularly, the present invention relates to a novel SDH, a novel SNDH, a DNA encoding same, an expression vector containing said DNA, a host cell transformed (transfected) with said expression vector, and the production of the SDH and SNDH by culturing the host cell.

The SDH and SNDH of the present invention are enzymes useful for producing 2-keto-L-gulonic acid.

BACKGROUND ART

2-Keto-L-gulonic acid (hereinafter referred to as 2KLGA) is a key intermediate in the synthesis of L-ascorbic acid. For industrial production, 2KLGA is chemically synthesized from L-sorbose by oxidation according to the Reichstein's method.

On the other hand, it is well known that many microorganisms have an ability to convert L-sorbose to 2KLGA through a two-step enzymatic oxidation by SDH and SNDH. Namely, SDH catalyzes the oxidation of L-sorbose to L-sorbosone, and SNDH catalyzes the oxidation of L-sorbosone to 2KLGA. However, because of the low productivity of 2KLGA obtained by using these microorganisms, they have not been applied to the industrial production yet.

It is desirable to provide efficient and simplified methods for the production of 2KLGA.

DISCLOSURE OF THE INVENTION

In an attempt to accomplish the above-mentioned objects, the inventors of this invention conducted intensive studies to find an SDH and an SNDH having preferable properties, and succeeded in producing a novel SDH and a novel SNDH having desirable properties for producing 2KLGA and developed the studies, which resulted in the completion of the present invention.

Accordingly, the present invention relates to a novel SDH derived from *Gluconobacter oxydans* T-100 (FERM BP-4188), which is characterized by:

(1) an ability to catalyze the conversion of L-sorbose into L-sorbosone, (2) a molecular weight of 58,000 dalton (SDS-PAGE), and (3) an N-terminal amino acid sequence of Thr—Ser—Gly—Phe—Asp—Tyr—Ile—Val—Val—Gly—Gly—Gly—Ser—Ala(SEQ ID NO: 5). Further, the present invention relates to an SDH having an amino acid sequence shown in the Sequence Listing, Sequence No. 1 to be mentioned later.

The present invention also relates to a novel SNDH derived from *Gluconobacter oxydans* T-100, which is characterized by:

(1) an ability to catalyze the conversion of L-sorbosone into 2KLGA, (2) a molecular weight of 50,000 dalton (SDS-PAGE), and (3) an N-terminal amino acid sequence of Asn—Val—Val—Ser—Lys—Thr—Val—Xaa—Leu (SEQ ID NO: 6, Xaa being an unidentified amino acid). The present invention further relates to an SNDH having an amino acid sequence shown in the Sequence Listing, Sequence No. 2.

The present invention also relates to a DNA which encodes the above-mentioned SDH and/or SNDH, an expression vector which contains said DNA, a host cell transformed (transfected) by said expression vector and a process for producing the SDH and/or SNDH, which comprises culturing said host cell (transformant) in a medium and recovering the SDH and/or SNDH from the resulting culture.

The *Gluconobacter oxydans* T-100 to be used in the present invention is a 2KLGA-high-producing mutant derived from *Gluconobacter oxydans* G716 (wild strain) by N-methyl-N'-nitro-N-nitrosoguanidine (NTG) mutagenesis in a conventional manner.

The *Gluconobacter oxydans* G716 was isolated from a persimmon, and has the following morphological and physiological properties. The method described in Bergey's Manual of Systematic Bacteriology Vol. 1 (1984) and the method described in Manual for Identification to Medical Bacteria (S. T. Cowan, 2nd. Edition, 1985) were principally employed for the taxonomic study.

1. Morphological properties

The *Gluconobacter oxydans* G716 is a Gram-negative, motile bacterium. The cell shapes are rod, occurring both singly and in pairs, and rarely in chains. Morphological characteristics of *Gluconobacter oxydans* G716

| | |
|---|---|
| Gram stain | negative |
| color of colony | pale |
| spore | negative |
| cell shape | rod |
| motility | positive |
| flagella | 3–8 polar flagella |

2. Physiological characteristics

Physiological characteristics of the *Gluconobacter oxydans* G716 are summarized in the following table.

Physiological characteristics of *Gluconobacter oxydans* G716

| Conditions | Characteristics |
|---|---|
| growth in air | + |
| at 4° C. | − |
| at 22° C. | + |
| at 30° C. | + |
| at 40° C. | − |
| catalase | + |
| oxidase | − |
| gelatin liquefaction | − |
| nitrate reduction | − |

-continued

| Conditions | Characteristics |
|---|---|
| aesuclin hydrolysis | − |
| acid formation | |
| L-arabinose | + |
| D-cellobiose | + |
| Dulcitol | + |
| D-galactose | + |
| D-glucose | + |
| glycerol | + |
| D-mannitol | + |
| D-mannose | + |
| D-xylose | + |
| D-lactose | − |
| maltose | − |
| D-raffinose | − |
| rhamnose | − |
| D-sorbitol | − |
| sucrose | − |
| D-trehalose | − |
| mol% G + C of the DNA | 60.0 |
| Ubiquinone | Q10 |

The organism is aerobic, showing no growth under anaerobic conditions. Optimum temperature is 22 to 30° C., showing no growth at 40° C. and 4° C. The best medium for growth is SY medium that is composed of 2.5% sorbitol and 0.5% yeast extract (pH 6.4). Strong ketogenesis occurs from glucose and glycerol.

The *Gluconobacter oxydans* T-100 to be used in the present invention has the morphological and physiological properties identical to those of *Gluconobacter oxydans* G716.

The new SDH and new SNDH of the present invention can be prepared by recombinant DNA technology, polypeptide synthesis and the like.

In case where recombinant DNA technology is employed, the new SDH and/or new SNDH can be prepared by culturing a host cell transformed (transfected) with an expression vector containing a DNA encoding the amino acid sequence of the new SDH and/or new SNDH in a nutrient medium and recovering the same from the obtained culture.

Particulars of this process are explained in more detail in the following.

The host cell includes, for example, microorganisms such as bacteria (e.g. *Escherichia coli, Gluconobacter oxydans* and *Bacillus subtilis*), yeast (e.g. *Saccharomyces cerevisiae*), animal cell lines and cultured plant cells. Preferred examples of the microorganisms include bacteria, especially strains belonging to the genus Escherichia (e.g. *E. coli* JM109 ATCC 53323, *E. coli* NM538 ATCC 35638, *E. coli* HB101 ATCC 33694, *E. coli* HB101-16 FERM BP-1872 and *E. coli* 294 ATCC 31446) and the genus Bacillus (e.g. *Bacillus subtilis* ISW1214), yeast, especially strains belonging to the genus Saccharomyces (e.g. *Saccharomyces cerevisiae* AH22), and animal cell lines [e.g. mouse L929 cell and Chinese hamster ovary (CHO) cell].

When a bacterium, especially *E. coli* or *Bacillus subtilis* is used as a host cell, expression vector is usually composed of at least promoter, initiation codon, DNA encoding amino acid sequence(s) of the new SDH and/or new SNDH, termination codon, terminator region, and replicatable unit.

When a yeast or an animal cell is used as a host cell, the expression vector is preferably composed of at least promoter, initiation codon, DNA encoding amino acid sequences of signal peptide and the new SDH and/or new SNDH and termination codon, and it is possible that enhancer sequence, 5'- and 3'-noncoding region of the new SDH, 5'- and 3'-noncoding region of the new SNDH, splicing junctions, polyadenylation site and replicatable unit are also inserted.

The promoter for expressing the new SDH and/or new SNDH in bacteria comprises, for example, promoter and Shine-Dalgarno (SD) sequence (e.g. AAGG). Preferable promoters include, for example, conventionally employed promoters (e.g. PL-promoter and trp-promoter for *E. coli*) and promoter of the SNDH chromosomal gene.

The promoters for expressing the new SDH and/or new SNDH in yeast include, for example, the promoter of the TRP1 gene, the ADHI or ADHII gene, and acid phosphatase (PH05) gene for *S. cerevisiae*.

The promoters for expressing the new SDH and/or new SNDH in mammalian cells include, for example, SV40 early or late-promoter, HTLV-LTR-promoter, mouse metallothionein I (MMT)-promoter and vaccinia-promoter.

Preferable initiation codon includes, for example, methionine codon (ATG).

The signal peptide includes, for example, signal peptides of other enzymes conventionally employed (e.g. signal peptide of the native t-PA and signal peptide of the native plasminogen).

The DNA encoding the signal peptide or the new SDH and/or new SNDH can be prepared in a conventional manner, such as a partial or whole DNA synthesis using DNA synthesizer and a method comprising preparing from *Gluconobacter oxydans* genomic DNA in a conventional manner such as PCR procedure or DNA probe procedure described in Molecular Cloning (mainly in Chapters 11 and 14, Cold Spring Harbor Laboratory Press, 1989, USA).

The termination codon includes, for example, conventionally employed termination codons (e.g. TAG and TGA).

The terminator region includes, for example, natural or synthetic terminator (e.g. terminator of the new SDH chromosomal gene and synthetic fd phage terminator).

The replicatable unit is a DNA compound capable of replicating the whole DNA sequence belonging thereto in host cell, and may include natural plasmid, artificially modified plasmid (e.g. DNA fragment prepared from natural plasmid) and synthetic plasmid. In the present invention, the replicatable unit can be appropriately selected according to the microorganism to be used as a host cell. Preferable examples of the plasmid include plasmid pBR322 and artificially modified plasmid thereof (DNA fragment obtained from a suitable restriction enzyme treatment of pBR322) for *E. coli*, yeast 2 μ plasmid and yeast chromosomal DNA for yeast, plasmid pRSVneo ATCC 37198, plasmid pSV2dhfr ATCC 37145, plasmid pdBPV-MMTneo ATCC 37224 and plasmid pSV2neo ATCC 37149 for mammalian cells.

The enhancer sequence includes, for example, the enhancer sequence (72 b.p.) of SV40.

The polyadenylation site includes, for example, the polyadenylation site of SV40.

The splicing junction includes, for example, the splicing junction of SV40.

The promoter, initiation codon, DNA encoding amino acid sequence of the new SDH and/or new SNDH, termination codon(s) and terminator region can consecutively and circularly be linked with an adequate replicatable unit (plasmid), using, if desired, adequate DNA fragment(s) in a conventional manner (e.g. digestion with restriction enzyme, ligation using T4 DNA ligase) to give the expression vector of the present invention.

When mammalian cells are used as host cells, it is possible that enhancer sequence, promoter, 5'-noncoding region of the cDNA of the new SDH and/or new SNDH, initiation codon, DNA encoding the signal peptide, DNA encoding amino acid sequence(s) of the new SDH and/or new SNDH, termination codon(s), 3'-noncoding region of the cDNA of the new SDH and/or new SNDH, splicing junctions and polyadenylation site are consecutively and circularly linked with an adequate replicatable unit in the above manner to give an expression vector.

The transformant of the present invention can be prepared by introducing the expression vector obtained above into a host cell. Introduction of the expression vector into the host cell (transformation, hereinafter used as also meaning transfection) can be carried out in a conventional manner (e.g. Kushner method for *E. coli*, calcium phosphate method for mammalian cells and microinjection).

For the production of the new SDH and/or new SNDH by the process of this invention, the thus-obtained transformant containing the expression vector is cultured in an aqueous nutrient medium.

The nutrient medium to be used may contain carbon source(s) (e.g. glucose, glycerine, mannitol, fructose and lactose) and inorganic or organic nitrogen source(s) (e.g. ammonium sulfate, ammonium chloride, hydrolysate of casein, yeast extract, polypeptone, Bactotrypton and beef extract). If desired, other nutritious sources such as inorganic salts (e.g. sodium or potassium biphosphate, dipotassium hydrogen phosphate, magnesium chloride, magnesium sulfate and calcium chloride), vitamins (e.g. vitamin $B_1$), and antibiotics (e.g. ampicillin, kanamycin) may be added to the medium. For the culture of mammalian cells, Dulbecco's Modified Eagle's Minimum Essential Medium (DMEM) supplemented with fetal calf serum and antibiotic is often used.

The culture of the tranformant is usually carried out at pH 5.5–8.5 (preferably pH 7–7.5) and 18–40° C. (preferably 20–30° C.) for 5–50 hours.

When the thus-produced new SDH and/or new SNDH exist(s) in the culture solution, culture filtrate (supernatant) is obtained by filtration or centrifugation of the culture. The new SDH and/or new SNDH can be purified from the culture filtrate by a method generally employed for the purification and isolation of natural or synthetic proteins (e.g. dialysis, gel filtration, affinity column chromatography using anti-SDH monoclonal antibody or anti-SNDH monoclonal antibody, column chromatography on a suitable adsorbent and high performance liquid chromatography).

When the produced new SDH and/or new SNDH exist(s) in periplasm and cytoplasm of the cultured transformant, cells are collected by filtration and centrifugation, and the cell wall and/or cell membrane thereof are/is destroyed by, for example, treatment with supersonic waves and/or lysozyme to give debris. The debris can be dissolved in a suitable aqueous solution (e.g. 8 M aqueous urea and 6 M aqueous guanidium salt). From the solution, the new SDH and/or new SNDH can be purified in a conventional manner as exemplified above.

If it is necessary to refold the new SDH and/or new SNDH produced in *E. coli* by the method of the present invention, the refolding can be carried out in a conventional manner.

If the SDH activity and/or new SNDH activity exist(s) in the transformant, the following can be exemplified as the materials obtained by processing the culture (hereinafter the material is referred to as processed material).

(1) Raw cells: separated from the culture in a conventional manner such as filtration and centrifugation:

(2) dried cells: obtained by drying said raw cells of (1) above in a conventional manner such as lyophilization and vacuum drying;

(3) cell-free extract: obtained by destroying said raw cells of (1) above or dried cells of (2) above in a conventional manner (e.g. autolysis of the cells using an organic solvent, grinding the cells with alumina, sea sand etc., and treating the cells with supersonic waves);

(4) enzyme solution: obtained by purification or partial purification of said cell-free extracts of (3) above in a conventional manner (e.g. column chromatography); and (5) immobilized cells or enzyme: prepared by immobilizing said raw cells of (1) above or dried cells of (2) above or the enzyme of (4) above in a conventional manner (e.g. a method using acrylamide, glass bead, ion exchange resin etc.).

If the SDH activity and/or new SNDH activity exist(s) in a culture filtrate of the transformant, the culture filtrate (supernatant), purified enzyme solution and immobilized enzymes can be exemplified as the processed materials of the culture.

The assay of the new SDH activity in crude mixture such as sonicated cell lysate or its processed material obtained in each purification step can be usually conducted according to T. SUGISAWA et al. (Agric. Biol. Chem., 55, 363–370, 1991) using L-sorbose as a substrate and 2,6-dichlorophenolindophenol (hereinafter referred to as DCIP) as an electron acceptor in phosphate buffer (pH 7.0). The enzyme activity is measured as the reduction rate of DCIP, which is determined by the decrease of absorbance at 600 nm. One enzyme unit is defined as the amount of the enzyme that catalyzes the reduction of 1 $\mu$mol DCIP per minute. Preferable pH of the reaction mixture, concentration of L-sorbose and DCIP, reaction time and reaction temperature may vary with the medium or its processed material to be used. Generally, the reaction is carried out at pH 7 to 10, preferably pH 8 to 9, at 5 to 50° C., preferably 20 to 45° C. for 0.5 to 24 hours.

The new SDH enzyme activity may be also assayed by determining the amount of the reaction product, L-sorbosone labelled with benzamidine hydrochloride, using post column high performance liquid chromatography (HPLC) with fluorescent detection (Ex. 315 nm, Em. 405 nm).

The activity of novel SNDH present in crude mixtures, such as ultrasonication cell lysate and treated substances obtained in respective purification steps, can be also assayed by a general method by SUGISAWA et al. (Agric. Biol. Chem., 55, 363–370, 1991). In this case, SNDH activity is assayed by measuring the amount of NADH produced using nicotinamido adenine dinucleotide (hereinafter referred to as AND) as an electron acceptor and L-sorbosone as a substrate in phosphate buffer (pH 7.0), which is determined by the absorbance at 340 nm. One enzyme unit is defined as the amount of the enzyme that produces 1 $\mu$mol NADH per minute. Preferable pH of the reaction mixture, concentrations of L-sorbosone and AND to be used, reaction time and reaction temperature may vary with a medium and processed materials to be used. Generally, the reaction is carried out at pH 7 to 10, preferably pH 8 to 9, at 5 to 50° C., preferably 20 to 45° C. for 0.5 to 24 hours.

The new SDH and new SNDH of the present invention are enzymes having preferable properties useful for producing 2KLGA, and therefor L-ascorbic acid. According to the present invention, the new SDH and new SNDH having such preferable properties can be produced in large amounts by genetic engineering.

Figure 1:
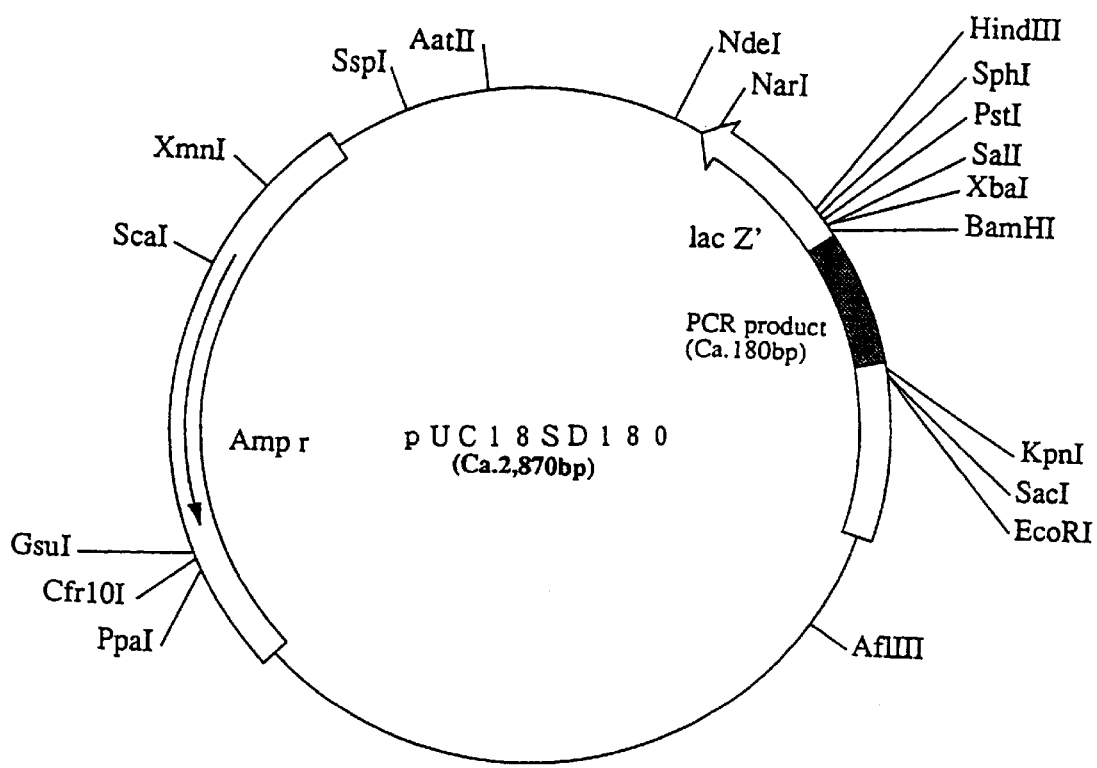
FIG. 1 is a restriction enzyme map of pUC18SD180.

The present invention is explained in more detail in the following. In the following Examples, plasmids, enzymes such as restriction enzyme, T4 DNA ligases, and other materials were obtained from commercial sources and used according to the indication by suppliers. Operations employed for the cloning of DNA, transformation of host cells, cultivation of transformants, recovery of the new SDH and/or new SNDH from the obtained culture, and the like are well known in the art or can be adapted from literatures.

It is needless to say that the present invention is not limited to these Examples.

EXAMPLE 1

Purification of SDH from *Gluconobacter oxydans* T-100

(1) Microorganism

*Gluconobacter oxydans* T-100 was selected as a 2KLGA-high-producing mutant derived from *Gluconobacter oxydans* G716 (wild strain) by nitrosoguanidine mutagenesis.

(2) Cultivation of *Gluconobacter oxydans* T-100

Single colonies of *Gluconobacter oxydans* T-100 were transferred into 6 independent culture media (100 ml each) consisting of 2.5% glucose, 1.0% polypeptone, 0.5% yeast extract (Difco Labs., USA) and 2.0% $CaCO_3$ in 500 ml Erlenmeyer flasks. The cultivation was performed at 30° C. on a rotary shaker (250 rpm) for 18 hours. The cultivated medium (total 600 ml) was inoculated to 20 liters of a fermentation medium containing 5% D-sorbitol, 0.5% glycerol, 0.5% yeast extract and 1.0% $CaCO_3$ in a 30 L jar. Cultivation was carried out at 30° C. for 42 hours under aeration at 20 liters/minute and agitation at 300 rpm. The cultivated broth (20 L) was centrifuged at 6,000 rpm at 4° C. for 10 minutes. The cells were washed once with cold saline and recentrifuged under the same conditions. The cells were stored at −20° C. until use.

(3) Preparation of the membrane fraction

Cells (17.7 g, wet weight) obtained in (2) were suspended in 50 ml of 10 mM phosphate buffer (pH 7.0), disrupted by sonication, and centrifuged at 8,000 rpm at 4° C. for 10 min to give a supernatant. On the other hand, the resulting precipitates were suspended in 40 ml of 10 mM phosphate buffer (pH 7.0), sonicated for disruption and centrifuged under the same conditions as above. The supernatants were pooled and ultracentrifuged at 32,000 rpm at 4° C. for one hour. The resulting precipitates were washed once with phosphate buffer (50 ml) and subjected to ultracentrifugation under the same conditions as above to give crude membrane proteins (membrane fraction).

(4) Solubilization of SDH from the membrane fraction

The membrane fraction obtained in (3) was suspended in 50 ml of 10 mM phosphate buffer (pH 7.0). To the suspension, 0.75 ml of 20% Triton X-100 (Nacalai Tesque, Japan) and 1.8 g of L-sorbose were added, and the mixture was stirred on ice for 3.5 hours. The resultant suspension was ultracentrifuged at 32,000 rpm at 4° C. for one hour to give a supernatant (ca. 48 ml), designated as solubilized SDH fraction.

(5) Ion-exchange chromatography

The solubilized fraction (16 ml) obtained in (4) was subjected to ion-exchange chromatography on a TSKgel DEAE-5PW column (7.5 mm inner diameter×75 mm, Toso Co. Ltd., Japan) equilibrated with 10 mM phosphate buffer (pH 7.0) containing 0.3% Triton k-100 and 200 mM L-sorbose. The column was eluted with a linear gradient of sodium chloride from 0 M to 0.5 M in an equilibration buffer. Enzyme activity was assayed according to T. SUGISAWA et al. (Agric. Biol. Chem., Vol. 55, 363–370, 1991) using L-sorbose as a substrate and 0.1 mM 2,6-dichlorophenolindophenol (DCIP) as an electron acceptor in 0.28 M phosphate buffer (pH 7.0). One enzyme unit was defined as the amount of the enzyme that catalyzes the reduction of 1 μmole DCIP per minute. The reduction of DCIP was determined by the decrease of absorbance at 600 nm with spectrophotometer (Model UV-160, Shimadzu, Japan). Active fractions were pooled, diluted 3-fold with 10 mM phosphate buffer (pH 7.0), and applied to a DEAE-TOYOPEARL 650 M column (7.0 mm inner diameter ×17 mm, Toso Co. Ltd., Japan) equilibrated with 10 mM phosphate buffer (pH 7.0). The column was eluted with 0.2 M sodium chloride in an equilibration buffer. The resulting eluate was used for further purification steps.

(6) Gel-filtration chromatography

A portion (300 μl) of the concentrated active fraction was subjected to gel-filtration chromatography on a Superose 12 HR10/30 column (10 mm inner diameter×30 cm, Pharmacia, Sweden) equilibrated with 10 mM phosphate buffer (pH 7.0) containing 0.3% Triton X-100, 200 mM L-sorbose and 0.2 M sodium chloride. Elution was performed using the same buffer. Each fraction (0.4 ml) was analyzed by polyacrylamide gel electrophoresis in the presence of sodium dodecyl sulfate (SDS-PAGE, 12.5% gel) and by enzyme assay described in Example 1 (5). From the analysis of SDS-PAGE, SDH activity was found to correspond to 58 kd protein, suggesting that the 58 kd protein was the desired SDH molecule.

EXAMPLE 2

Amino acid sequence analysis of SDH

The concentrated active fraction (15 μl) was subjected to SDS-PAGE (12.5% gel) and the separated proteins were blotted on a polyvinylidene difluoride (PYDF) membrane. The membrane containing 58 kd protein stained by ponceau S was cut out and washed with distilled water. The membrane piece was directly sequenced with an automated protein sequencer Model 470A (Applied Biosystems Inc., USA) for N-terminal amino acid sequence analysis.

To determine the internal amino acid sequence, fragmentation with achromobacter protease I (Wako Chemical, Japan) was carried out on the surface of the membrane. The fragments obtained were eluted with 50 mM Tris-HCl (pH 9.0) containing 8% acetonitrile, and separated by reversed phase chromatography using Cosmosil 5C4-300 (4.6 mm inner diameter×50 mm, Nacalai Tesque, Japan) with a linear gradient elution (75 min) of acetonitrile of from 8% to 83% in 0.05% trifluoroacetic acid. Two kinds of peptides (Peptide 1 and Peptide 2) were isolated, and sequenced with an automated protein sequencer Model 470A for amino acid sequence identification. The resultant data are shown in Table 1(SEQ ID NO: 5,7,8).

TABLE 1

| $NH_2$-terminal sequence | TSGFDYIVVGGGSA |
|---|---|
| Peptide 1 | MTTGPHTWDLLTEPQK |
| Peptide 2 | LMMLSGVGPA |

EXAMPLE 3

Preparation of DNA probe (1) Synthesis of DNA oligomers

Each oligonucleotide listed in Table 2 below was synthesized by phospho amidite method using DNA synthesizer model 392 (Applied Biosystems Inc., USA). The synthesized oligonucleotide was liberated from CPG polymer support (CPG: controlled pore glass) with 28% aqueous ammonia, followed by heating at 60° C. for 9 hours to remove all protective groups. The reaction mixture was evaporated in vacuo, and the residue was dissolved in 200 μL of TE [10 mM Tris-HCl (pH 7.4)-1 mM EDTA]. The resulting solution was washed once with ether and precipitated with ethanol. The obtained oligonucleotides were used as primers for polymerase chain reaction without further purification (SEQ ID NO: 9,10).

TABLE 2

Oligonucleotide encoding $NH_2$-terminal sequence (forward primer)
  5'> ACC (TA)(GC)C GGC TT(TC) GA(TC) TA(TC) AT(TCA) GT <3'

Oligonucleotide encoding internal Sequence (reverse primer)
  5'> TC CCA (ATCG)GT (AG)TG (ATCG)GG (ATCG)CC <3'

(2) Preparation of chromosomal DNA

A single colony of Gluconobacter oxydans T-100 was cultivated in a medium (100 ml) consisting of 2% glucose, 1% polypeptone and 0.5% yeast extract at 37° C. for 24 hours. The cells were collected by centrifugation (4,600 rpm, 10 min) and suspended in TE buffer (2.5 ml). A portion (2.0 ml) of the suspension was diluted with 20 ml of STE buffer [20% sucrose-50 mM Tris-HCl (pH 8)-1 mM EDTA], mixed with 5 ml of lysozyme solution (5 mg/ml), and incubated at 37° C. for 30 min. Sarcosil solution [1% lauroyl sarcosilate-100 mM EDTA (pH 9.0)] (50 ml) and proteinase K (40 mg) were added, and the mixture was incubated at 50° C. for 1.5 hours. Cesium chloride (93.8 g) and 6 ml of ethidium bromide (5 mg/ml) were dissolved in 75 ml of said mixture, and the cesium chloride solution was ultracentrifuged at 50,000 rpm at 20° C. for 14 hours. The portion containing chromosomal DNA was isolated, washed twice with isopropyl alcohol saturated with physiological saline, and dialyzed against TE buffer (2 L) for 4 hours. The dialysate was extracted with phenol (20 ml), and dialyzed twice against TE buffer (2 L) to give the desired chromosomal DNA solution (14 ml, 91.5 μg/ml).

(3) Polymerase chain reaction

Polymerase chain reaction (PCR) was carried out with 180 ng of *Gluconobacter oxydans* T-100 chromosomal DNA and 2.5 μmoles of each primer of Table 2, using Hybaid thermal reactor Model HB-TR1 (Hybaid Limited, UK). The reaction mixture [200 μM dNTPs each and 2.5 units Taq DNA polymerase in PCR buffer (Perkin Elmer-Cetus, USA)] was subjected to 50 cycles of PCR, each consisting of 0.5 min of denaturation at 95° C., 1 min of annealing at 42° C. and 2 min of polymerization at 72° C. A single fragment was obtained by PCR. The DNA fragment (180 bp) supposedly coding for a part of the SDH gene was isolated by 1.5% agarose gel-electrophoresis and filled with DNA polymerase Klenow fragment (Takara Shuzo, Japan) to give a blunt-ended DNA. The resultant DNA and pUC18 previously digested with SmaI (Nippon Gene, Japan) were ligated in the presence of T4 DNA ligase (Takara Shuzo, Japan). The ligation mixture was used to transform *E. coli* JM109 (Nippon Gene, Japan) according to the procedure of SHIGE-SADA et al. (Saibo-kogaku, 2, 616–626, 1983). From one of the transformants, the desired plasmid pUC18SD180 (see FIG. 1) was obtained and characterized by restriction mapping.

(4) Preparation of the $^{32}$P-labelled probe

The insert DNA (ca. 200 bp) was isolated by digestion of pUC18SD180 with BamHI and EcoRI (Nippon Gene, Japan). The ca. 200 bp DNA was purified by 0.5% agarose gel-electrophoresis. Purified DNA was $^{32}$P-labelled with nick translation kit (Takara Shuzo, Japan) according to the appended protocols. The specific activity of DNA labelled with 32p was about $3.7 \times 10^7$ cpm/μg.

EXAMPLE 4

Isolation of SDH gene from Gluconobacter oxydans T-100 DNA library (1) Preparation of chromosomal DNA library The genomic DNA obtained in Example 3 (2) was partially digested with MboI (Nippon Gene, Japan) and the fragments were separated on a sucrose gradient to produce a fragment with a size range of from 8 kbp to 22 kbp before cloning into the BamHI site of lambda phage vector EMBL-3 (Clonetech). This lambda phage vector was introduced into *E. coli* NM538 (Clonetech) to construct Gluconobacter T-100 chromosomal DNA library.

(2) Plaque hybridization

Preparation of lambda phage plaques with *E. coli* NM538 (Clonetech) as a plating bacterium and immobilization of the plaques on the nitrocellulose filter were carried out according to the protocols described in Molecular Cloning vol. 1, Chapter 2, page 108, 1989, USA. The filters containing the lambda DNA were incubated in a hybridization buffer (50% formamide-1% bovine serum albumin-0.1% polyvinyl pyrrolidone-0.1% ficoll-5 ×SSPE (see Molecular Cloning)-0.1% SDS-100 µg/ml salmon sperm DNA) at 42° C. for 4 hours, in the same buffer but containing $^{32}$P-labelled probe (ca. 200 bp, ca. 1×10$^7$ cpm/ml) at 42° C. for 18 hours and in 2×SSC (see Molecular Cloning) containing 0.05% SDS at 42° C. successively to remove the excess probe. The filters were exposed to an X-ray film HR-H (Fuji Film, Japan) at −80° C. for 18 hours. As a result of the first screening of lambda phage library, about 30 positive phages were obtained from 72,000 plaques.

(3) Southern blotting

Figure 2:
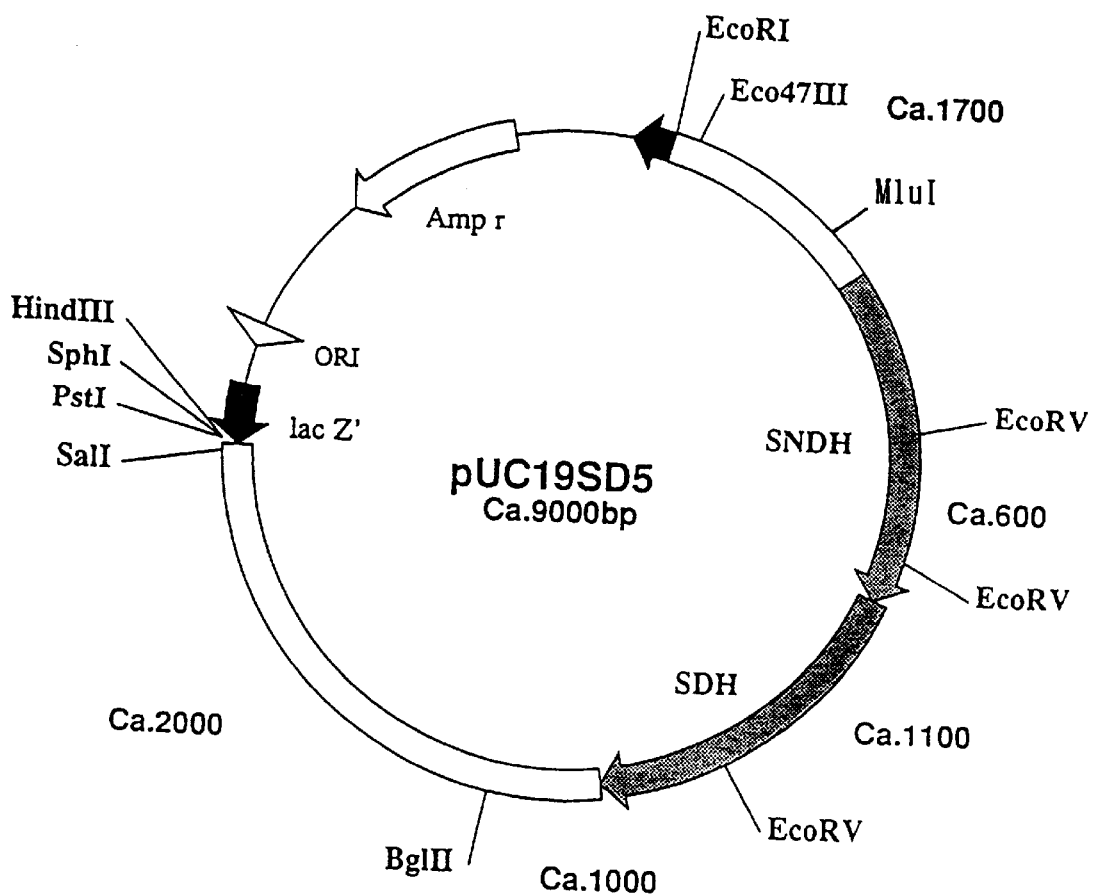
FIG. 2 is a restriction enzyme map of plasmid pUC19SD5 containing DNA encoding the novel SDH of the present invention and DNA encoding the novel SNDH of the present invention.
Figure 3:
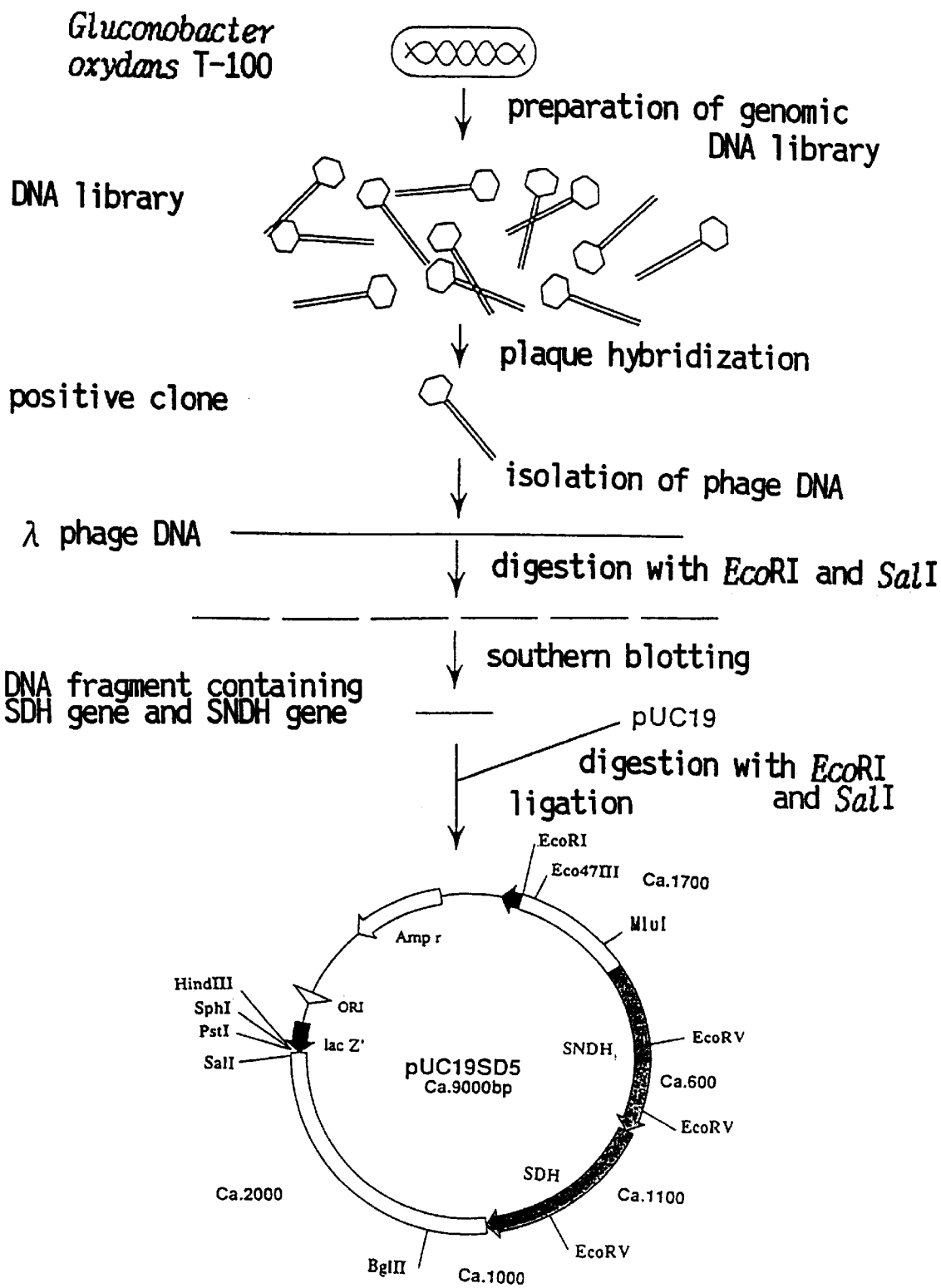
FIG. 3 shows the construction of plasmid pUC19SD5.

One of the positive phage DNAs was digested with EcoRI and SalI (Nippon Gene, Japan) and subjected to 0.8% agarose gel electrophoresis. The DNA fragments separated on the gel were transferred onto a nitrocellulose filter by electroblotting. Approximately 6 kbp DNA fragment was identified to hybridize the $^{32}$P-labelled probe. It was cloned into between the EcoRI site and SalI site of pUC19 (Nippon Gene, Japan) to give pUC19SD5 (FIG. 2).

EXAMPLE 5

DNA sequence analysis of SDH gene (1) Construction of the plasmids for DNA sequencing Construction of plasmid pSD5RRV pUC19SD5 was digested with EcoRV (Toyobo, Japan). From among the three bands separated by 1.5% agarose gel-electrophoresis, 1.1 kbp DNA which hybridizes the $^{32}$P-labelled probe was isolated and cloned into the SmaI site of pUC18 to give the plasmid pSD5RRV.

(2) Construction of plasmid pSD5RVS pUC19SD5 was digested with EcoRV and Eco47III (Toyobo, Japan). The large DNA (ca. 5,700 bp) was isolated and self-ligated with T4 DNA ligase (Takara Shuzo, Japan) to give the plasmid pSD5RVS.

(3) DNA sequence analysis

DNA sequence analysis of the template DNA (pSD5RRV and pSD5RVS) was performed by dideoxy termination method with 370A DNA sequencer (Applied Biosystems, USA) according to appended protocols. The M13 sequencing primers, universal and reverse primers (New England Biolabs, USA) were used for the first sequencing. Based on the DNA sequence determined by the first sequence analysis, the following primers were synthesized and used for further DNA sequence analyses. The synthesized primers used were as follows (SEQ ID NO: 11–15).

Primer 1 (12 mer): 5'>CTG TGT TCT CGC<3'

Primer 2 (15 mer): 5'>TCG GTT TCG CGA AGA<3'

Primer 3 (16 mer): 5'>CGT CTT CAA CGG AAC G<3'

Primer 4 (16 mer): 5'>GGA GTG ACG TCC GTT C<3'

Primer 5 (16 mer): 51'>GAG ATG TTC TCC CAG C<3'

As a result of the analysis, an open reading frame (ORF) consisting of 1596 base pairs was found. The amino acid sequence encoded by the nucleotide sequence beginning from the initiation codon (ATG) of the ORF coincided with the amino acid sequence of SDH which was obtained in Example 2, and the theoretical molecular weight of the protein encoded by the ORF, of 58 kd coincided well with the apparent molecular weight of SDH, 58 kd by SDS-PAGE. Therefore, the ORF was determined to be the SDH gene.

The nucleotide sequence of the SDH gene is shown in the Sequence Listing, Sequence No. 3 to be mentioned later, and the amino acid sequence deduced from the nucleotide sequence is shown in Sequence No. 1.

EXAMPLE 6

Expression of SDH gene in E. coli (1) Cultivation of the transformed (transfected) E. coli A single colony of E. coli JM109 transformed with pUC19SD5 (E. coli JM109-pUC19SD5) was inoculated into 100 ml of a medium containing 1% Bactotrypton (Difco Labs., USA), 0.5% yeast extract, 0.5% sodium chloride and 0.1% glucose (pH 7.2) in a 500 ml flask and cultivated at 30° C. for 18 hours. A portion of the cultured broth (3 ml of each) was transferred to two media containing 1% Bactotrypton, 0.5% yeast extract, 0.5% sodium chloride, 1% glycerol, 0.3% $KH_2PO_4$, 0.8% $Na_2PO_4.12H_2O$ (pH 6.8), 1% L-sorbose and 100 µg/ml of ampicillin in a 500 ml Erlenmeyer flask. The resultant mixtures were cultivated at 25° C. for 3 days. The cultured broth (total 200 ml) was harvested by centrifugation at 6,000 rpm at 4° C. for 10 minutes. The cells were washed twice with saline, suspended in 5 ml of the same solution, and disrupted by sonication at 30 second intervals for a total sonication time of 2 minutes under ice-cooling. The resultant cell lysate was stored at −20° C. until use for an enzyme assay.

(2) Assay of SDH activity

SDH expressed activity was assayed by determining the amount of the reaction product, L-sorbosone, using high performance liquid chromatography (HPLC). The reaction mixture consisting of 1% L-sorbose, 1 mM phenazine methosulfate, 0.1 M phosphate buffer (pH 8.0) and the sonicated cell lysate was incubated at 30° C. with shaking for 5 hours. The reaction was stopped by adjusting pH to 2 with 6 N sulfuric acid. The reaction mixture was centrifuged at 6,000 rpm at 4° C. for 10 minutes and a portion of the supernatant was directly analyzed by HPLC with a #3011 N column (4.6 mm inner diameter×300 mm, Hitachi, Japan). The mobile phase was 1 M borate buffer (pH 9.5) containing 0.02 M benzamidine hydrochloride and 0.25 M potassium sulfate which were used for a post column labelling method, at a flow rate of 0.8 ml per minute. The post column labelling reaction was performed at 80° C. in a Tefron tube (0.5 mm inner diameter×10 m). Detection of the labelled compound was carried out by monitoring fluorescence (Ex. 315 nm, Em. 405 nm). As shown in the following Table 3, the sonicated cells containing plasmid pUC19SD5 had an ability to convert L-sorbose to L-sorbosone. However, no activity was found in the cell lysate treated at 100° C. or the cells without the plasmid. These results indicate that the recombinant plasmid pUC19SD5 contains the gene encoding L-sorbose dehydrogenase, which expressed in E. coli JM109.

TABLE 3

| Strain | Treatment | L-sorbosone (μg/ml) |
|---|---|---|
| JM109 (pUC19SD5) | Sonication | 2,310 |
| JM109 (pUC19SD5) | Sonication, boiling | 24 |
| JM109 | Sonication | 21 |
| Basal | — | 33 |

EXAMPLE 7

Purification of SNDH from *Gluconobacter oxydans* T-100

(1) Preparation of crude enzyme solution

The cells (ca. 10 g, wet weight) obtained in Example 1 (2) were suspended in 40 ml of 10 mM phosphate buffer (pH 7.0) under ice-cooling, disrupted by sonication, and centrifuged at 8,000 rpm at 4° C. for 10 min. The supernatant was ultracentrifuged at 32,000 rpm at 4° C. for one hour. The resulting supernatant was used for further determinations as an SNDH crude enzyme solution.

(2) Ion-exchange chromatography

The SNDH crude enzyme solution (45 ml) was passed through QAE-TOYOPEARL 550 C column (1.6 cm inner diameter×30 cm, Toso Co. Ltd., Japan) previously equilibrated with 10 mM phosphate buffer (pH 7.0). The column was washed with the same buffer and eluted with a linear gradient of sodium chloride of from 0 M to 0.4 M in the same buffer. The activity of the enzyme was assayed by the method by SUGISAWA et al. (Agric. Biol. Chem., 55, 665–670, 1991), by measuring the amount of NADH produced by the reaction in the presence of 13.7 μM L-sorbosone and 0.73 μM AND in 50 mM phosphate buffer, which was determined by the absorbance at 340 nm. The active fractions (ca. 15 ml) were pooled and diluted 5-fold with phosphate buffer for use in the purification step to follow.

(3) Blue Sepharose chromatography

The enzyme solution (ca. 75 ml) obtained in (2) was passed through Blue Sepharose column (1.0 cm inner diameter×7 cm, Pharmacia, Sweden) previously equilibrated with phosphate buffer. The column was washed with the same buffer and eluted with a linear gradient of sodium chloride of from 0 M to 0.6 M in the same buffer. The respective fractions were analyzed by polyacrylamide gel electrophoresis in the presence of sodium dodecyl sulfate (SDS-PAGE) and by enzyme assay of Example 7 (2). As a result, it was found that the protein having a molecular weight of 50 kd by SDS-PAGE corresponded to the enzyme activity, suggesting that said 50 kd protein was the desired SNDH molecule.

EXAMPLE 8

SNDH amino acid sequence analysis

The active fraction (75 μl) obtained in Example 7 (3) was subjected to SDS-PAGE and the separated protein was blotted on a polyvinylidene difluoride (PVDF) membrane. The membrane containing 50 kd protein stained by Coomassie Brilliant Blue was cut out and washed with distilled water. The membrane piece was sequenced with an automated protein sequencer Model 470A (Applied Biosystems Inc., USA) for N-terminal amino acid sequence analysis. The results are shown below wherein Xaa is an unidentified amino acid. N-terminal amino acid sequence (SEQ ID NO: 6):

Asn—Val—Val—Ser—Lys—Thr—Val—Xaa—Leu—

EXAMPLE 9

DNA sequence analysis of SDNH gene (1) Construction of plasmid for DNA sequence analysis The plasmid pUC19SD5 (FIG. 2) obtained in Example 4 (3) was digested with SalI (Nippon Gene, Japan) and EcoRV (Toyobo, Japan) and subjected to 0.8% agarose gel electrophoresis. Of the separated DNA fragments, the fragments of about 600 bp and 4,300 bp were separated from the gel. The former was inserted into SmaI site of pUC18 to construct pSD6RRV. The latter was filled with DNA polymerase Klenow fragment (Takara Shuzo; Japan) to give a blunt-ended SalI cleavage site, followed by self-ligation to construct circular plasmid pSD5RIRV. This plasmid pSD5RIRV was digested with EcoRI and MluI, and about 3,400 bp fragment was isolated. Blunting and circularizing in the same manner as above gave pSD5MRV.

(2) DNA sequence analysis

DNA sequence analyses of the template DNA (pSD5MRV, pSD6RRV and pSD5RRV used for SDH nucleotide sequence analysis) were performed by dideoxy termination method with 370A DNA sequencer (Applied Biosystems, USA). The M13 sequencing primers, universal and reverse primers (New England Biolabs, USA) were used for the first sequencing. Based on the DNA sequences determined by the first sequencing, the following primers were synthesized and used for further DNA sequence analyses. The synthesized primers used were as follows.

Primer 1 (15 mer); 5'>TGATGGAGAATGGCG<3'
Primer 2 (15 mer); 5'>GTAATCAGACCGACG<3'
Primer 3 (15 mer); 5'>TTCATTCTCGCATCC<3'
Primer 4 (15 mer); 5'>GATCTCACCTTTCGC<3'
Primer 5 (15 mer); 5'>CACGGATGTGAAGCC<3'
Primer 6 (15 mer); 5'>GATCCTGTGTGAGCG<3'
Primer 7 (15 mer); 5'>GCGATGTCATCACGG<3'

As the result of the above analyses, an open reading frame (ORF) consisting of 1497 bp was found in the upstream of 5'-side of SDH gene. The amino acid sequence encoded by the nucleotide sequence beginning from the initiation codon (ATG) of the ORF coincided with the N-terminal amino acid sequence of SNDH which was obtained in Example 8, and the theoretical molecular weight of the protein encoded by the ORF, of 53 kd coincided well with the molecular weight of SNDH, 50 kd by SDS-PAGE. Therefore, the ORF was considered to be the SNDH gene. The nucleotide sequence of the SNDH gene is shown in the Sequence Listing, Sequence No. 4 to be mentioned later, and the amino acid sequence deduced from the nucleotide sequence is shown in Sequence No. 2.

EXAMPLE 10

Expression of SNDH gene in *E. coli*

(1) Cultivation of the transformed *E. coli*

In the same manner as in Example 6, cell lysate of *E. coli* JM109-pUC19SD5 was obtained and stored at −20° C. until use for an enzyme assay.

(2) Assay of SNDH activity

SNDH expressed activity was assayed by determining the amount of the reaction product, 2KLGA, using HPLC. The reaction mixture consisting of 1% L-sorbosone, 0.5 mM AND, 0.1 M phosphate buffer (pH 8.0) and the sonicated cell lysate was incubated at 30° C. with shaking for 5 hours. The reaction was stopped by adjusting pH to 2 with 6 N sulfuric acid. The reaction mixture was centrifuged at 6,000 rpm at 4° C. for 10 min, and a portion of the supernatant was analyzed by HPLC (column Capcellpak $NH_2$; 4.6 mm inner diameter×250 mm, Shiseido, Japan). The mobile phase was 20 mM sodium phosphate buffer (pH 3.0) containing 30% acetonitrile at a flow rate of 1.2 ml per minute. Detection was carried out by measuring ultraviolet absorption at 210 nm.

As a result, the mixture containing the sonicated cell lysate of *E. coli* JM109-pUC19SD5 transformed with the plasmid pUC19SD5 produced 5690 μg/ml of 2KLGA, demonstrating the ability to convert L-sorbosone to 2KLGA. While the host of the transformant, *E. coli* JM109 itself had an ability to convert same into 2KLGA, its ability was about one-second (2170 μg/ml) of the ability possessed by the transformant, thus suggesting evident enhancement of the ability of the transformant to convert same into 2KLGA, that is, SNDH activity. Therefrom it was made clear that the recombinant plasmid pUC19SD5 had a gene encoding SNDH, and the ORF consisting of 1497 bp at the upstream of 5'-side of the SDH gene found in Example 9 was an SNDH gene.

Industrial Applicability

The SDH and SNDH of the present invention are useful enzymes having preferable properties in the production of 2-keto-L-gulonic acid, as well as L-ascorbic acid. According to the production method of the present invention, the SDH and SNDH having such preferable properties can be produced in large amounts by genetic engineering.

Deposit of microorganism

The cell strain used in the present invention, *Gluconobacter oxydans* T-100 (deposit number FERM BP-4188) has been deposited at National Institute of Bioscience and Human-Technology, Agency of Industrial Science and Technology, Japan, since February 15, 1993.

What is claimed is:

1. A recombinant L-sorbosone dehydrogenase having an amino acid sequence of SEQ ID NO: 2.

2. An L-sorbosone dehydrogenase produced by a process comprising:

culturing a host cell transformed by an expression vector containing a DNA encoding the L-sorbosone dehydrogenase having the amino acid sequence of SEQ ID NO: 2 in a culture medium; and isolating said L-sorbosone dehydrogenase from the culture medium.

* * * * *